United States Patent
Gamage

(10) Patent No.: US 8,857,264 B2
(45) Date of Patent: Oct. 14, 2014

(54) CATHETER DIE

(75) Inventor: Sisira Kankanam Gamage, Palo Alto, CA (US)

(73) Assignee: Amphenol Thermometrics, Inc., St. Marys, PA (US)

( * ) Notice: Subject to any disclaimer, the term of this patent is extended or adjusted under 35 U.S.C. 154(b) by 59 days.

(21) Appl. No.: 13/436,185

(22) Filed: Mar. 30, 2012

(65) Prior Publication Data

US 2013/0259964 A1 Oct. 3, 2013

(51) Int. Cl.
*G01L 9/06* (2006.01)
*A61B 5/02* (2006.01)

(52) U.S. Cl.
USPC ........... 73/721; 73/719; 73/725; 600/488

(58) Field of Classification Search
None
See application file for complete search history.

(56) References Cited

U.S. PATENT DOCUMENTS

| | | | |
|---|---|---|---|
| 3,624,714 A | 11/1971 | Frassrand | |
| 4,685,469 A | 8/1987 | Keller | |
| 4,886,070 A | 12/1989 | Demarest | |
| 5,483,994 A | 1/1996 | Maurer | |
| 5,701,905 A | 12/1997 | Esch | |
| 6,264,612 B1 | 7/2001 | McConnell et al. | |
| 6,959,608 B2 | 11/2005 | Bly et al. | |
| 7,007,551 B2 | 3/2006 | Zdeblick et al. | |
| 7,013,734 B2 | 3/2006 | Zdeblick et al. | |
| 7,017,420 B2 | 3/2006 | Kalvesten et al. | |
| 7,028,550 B2 | 4/2006 | Zdeblick et al. | |
| 7,066,031 B2 | 6/2006 | Zdeblick et al. | |
| 7,073,387 B2 | 7/2006 | Zdeblick et al. | |
| 7,111,518 B1 | 9/2006 | Allen et al. | |
| 7,265,429 B2 | 9/2007 | Wan | |
| 7,284,441 B2 | 10/2007 | Zdeblick | |
| 7,398,688 B2 | 7/2008 | Zdeblick et al. | |
| 7,539,003 B2 | 5/2009 | Ray et al. | |
| 7,642,115 B2 | 1/2010 | Eriksen et al. | |
| 7,762,138 B2 | 7/2010 | Zdeblick et al. | |
| 7,911,315 B2 | 3/2011 | Bradley | |
| 7,952,154 B2 | 5/2011 | Guo et al. | |
| 8,013,405 B2 | 9/2011 | Eriksen et al. | |
| 8,044,929 B2 | 10/2011 | Baldo et al. | |
| 2003/0199085 A1 | 10/2003 | Berger et al. | |
| 2005/0103114 A1 | 5/2005 | Bly et al. | |
| 2005/0121734 A1 | 6/2005 | Degertekin et al. | |
| 2005/0187487 A1 | 8/2005 | Azizkhan et al. | |
| 2006/0117871 A1 | 6/2006 | Wilner | |
| 2009/0203163 A1 | 8/2009 | Erkisen et al. | |
| 2010/0230768 A1 | 9/2010 | Legat et al. | |
| 2010/0308791 A1 | 12/2010 | Gowrishetty et al. | |
| 2011/0256652 A1 | 10/2011 | Guo et al. | |
| 2013/0220972 A1* | 8/2013 | Gamage | 216/39 |

* cited by examiner

*Primary Examiner* — Andre Allen
(74) *Attorney, Agent, or Firm* — Blank Rome LLP

(57) ABSTRACT

A catheter die is provided and includes an elongate body having first and second opposing end portions and an end face at the first one of the first and second opposing end portions. The elongate body defines a cavity within the first end portion with an interior facing surface of the cavity disposed to extend alongside at least a portion of the first end face. At least one or more piezoresistive pressure sensors are operably disposed proximate to the cavity.

23 Claims, 4 Drawing Sheets

CATHETER DIE

BACKGROUND OF THE INVENTION

The subject matter disclosed herein relates to a catheter die and a method of fabricating a catheter die for pressure sensing.

A pressure sensor measures pressure, typically of fluids, gases or liquids. Pressure is an expression of the force exerted by a fluid, and is usually stated in terms of force per unit area. A pressure sensor usually acts as a transducer in that it generates a signal as a function of the pressure applied. Such a signal may be provided as a current.

There are generally two categories of pressure sensors. These include force collector types, which generally use a force collector, such as a diaphragm, piston, bourdon tube, or bellows, to measure strain or deflection due to applied force or pressure over an area, and other types, which use other properties, such as density, to infer gas or liquid pressures. A piezoelectric pressure sensor is a force collector type of pressure sensor and uses the piezoelectric effect in certain materials, such as quartz, to measure the strain upon a sensing mechanism due to pressure.

BRIEF DESCRIPTION OF THE INVENTION

According to one aspect of the invention, a catheter die is provided and includes an elongate body having first and second opposing end portions and an end face at the first one of the first and second opposing end portions. The elongate body defines a cavity within the first end portion with an interior facing surface of the cavity disposed to extend alongside at least a portion of the first end face. At least one or more piezoresistive pressure sensors are operably disposed proximate to the cavity.

According to another aspect of the invention, a catheter die is provided and includes an elongate body having sidewalls, longitudinal first and second opposing end portions of the sidewalls and an end face at the first one of the longitudinal first and second end portions. The sidewalls have a longitudinal length that is substantially larger than any planar dimension of the end face. The elongate body defines a cavity having an interior facing surface proximate to the end face such that a portion of the end face is defined as a diaphragm with the interior facing surface being disposed alongside at least a portion of the end face. At least one or more piezoresistive pressure sensors are operably disposed proximate to the diaphragm and the cavity.

According to yet another aspect of the invention, a method of assembling a catheter die is provided and includes forming an elongate body having first and second opposing end portions and an end face at the first one of the first and second opposing end portions, the elongate body having a longitudinal length that is substantially larger than any planar dimension of the end face, defining a cavity within the first end portion such that an interior facing surface of the cavity is disposed alongside at least a portion of the end face and operably disposing a piezoresistive pressure sensor proximate to the cavity.

These and other advantages and features will become more apparent from the following description taken in conjunction with the drawings.

BRIEF DESCRIPTION OF THE DRAWINGS

The subject matter, which is regarded as the invention, is particularly pointed out and distinctly claimed in the claims at the conclusion of the specification. The foregoing and other features, and advantages of the invention are apparent from the following detailed description taken in conjunction with the accompanying drawings in which:

The detailed description explains embodiments of the invention, together with advantages and features, by way of example with reference to the drawings.

DETAILED DESCRIPTION OF THE INVENTION

Figure 1:
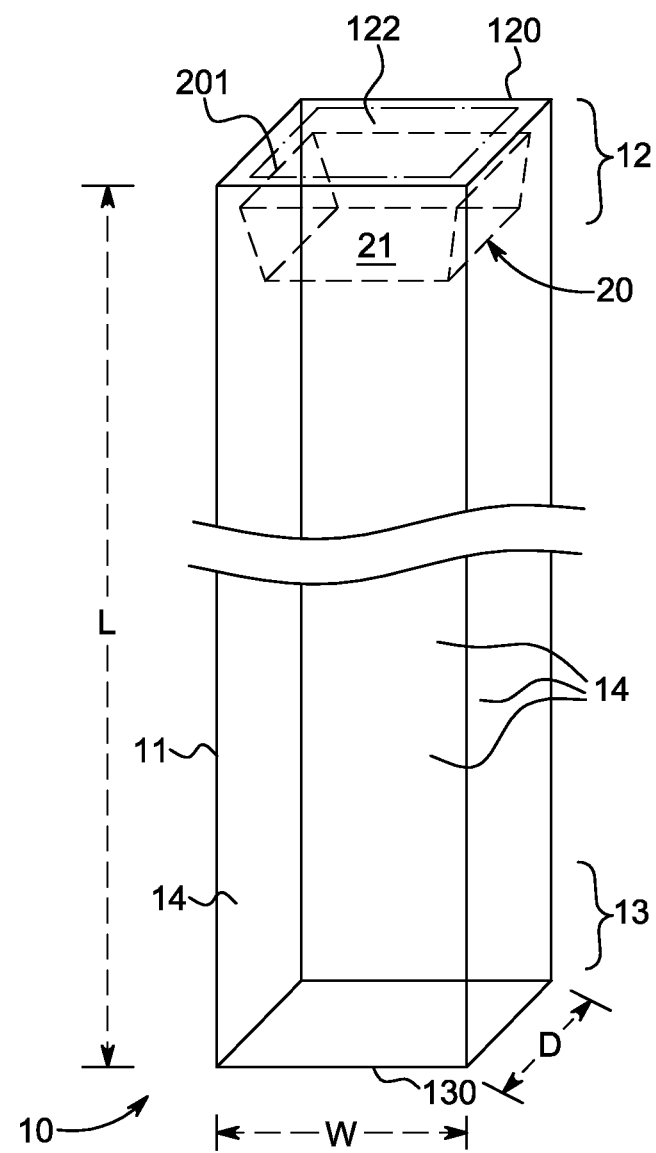
FIG. 1 is a perspective view of a catheter die in accordance with at least one embodiment.

FIG. 1 illustrates a catheter die 10 according to one aspect. The catheter die 10 includes a generally monolithic elongate body 11 having a first end portion 12 at which a first end face 120 is defined, a second end portion 13 opposite the first end portion 12 at which a second end face 130 is defined and sidewalls 14. The first and second end faces 120 and 130 each have planar width dimensions, W, and planar depth dimensions, D, which may be substantially similar to one another. The sidewalls 14 extend along a longitudinal length, L, of the elongate body 11. A magnitude of the longitudinal length, L, is substantially larger than respective magnitudes of either one of the planar width dimensions, W, or the planar depth dimensions, D, of the first and second end faces 120 and 130.

In accordance with embodiments, the elongate body 11 may be formed as a solid volumetric body with a substantially rectangular cross-section or, in some cases, a circular cross-section, an elliptical cross-section, a trapezoidal cross-section or a parallelipipedal cross-section with the planar width dimensions, W, and the planar depth dimensions, D, of the first and second end faces 120 and 130 being relatively shorter as compared to the longitudinal length, L, of the elongate body 11.

For example, the planar width dimension, W, and the planar depth dimension, D, of the first end face 120 may each be about 0.3-0.5 mm whereas the longitudinal length, L, of the elongate body 11 may be about 0.8-1.2 mm. As another example, a magnitude of the longitudinal length, L, may be 2.5-3.0 times the respective magnitudes of the planar width dimension, W, and the planar depth dimension, D, of the first end face 120 or the second end face 130.

The first end portion 12 of the elongate body 11 has a cavity 20 therein. The cavity 20 is defined in any one of various shapes such as, for example, an inverted frusto-trapezoidally shaped volume 21 that has a wide base proximate to the first end face 120 and a narrow end facing in a direction toward the second end portion 13. In any case, the cavity 20 may have an interior facing surface 201 proximate to the first end face 120 such that a portion of the first end face 120 opposing the interior facing surface 201 is defined as a diaphragm 122.

In accordance with embodiments, the interior facing surface 201 may be provided alongside at least a portion of the first end face 120. More particularly, a plane of the interior facing surface 201 may be disposed substantially in parallel with a plane of the first end face 120. In accordance with still further embodiments, a shape of the interior facing surface 201 (or any cross-section of the cavity 20) may be substantially similar to a shape of the end face 120. That is, if the end face 120 is rectangular, the interior facing surface 201 may be similarly rectangular.

Figure 2:
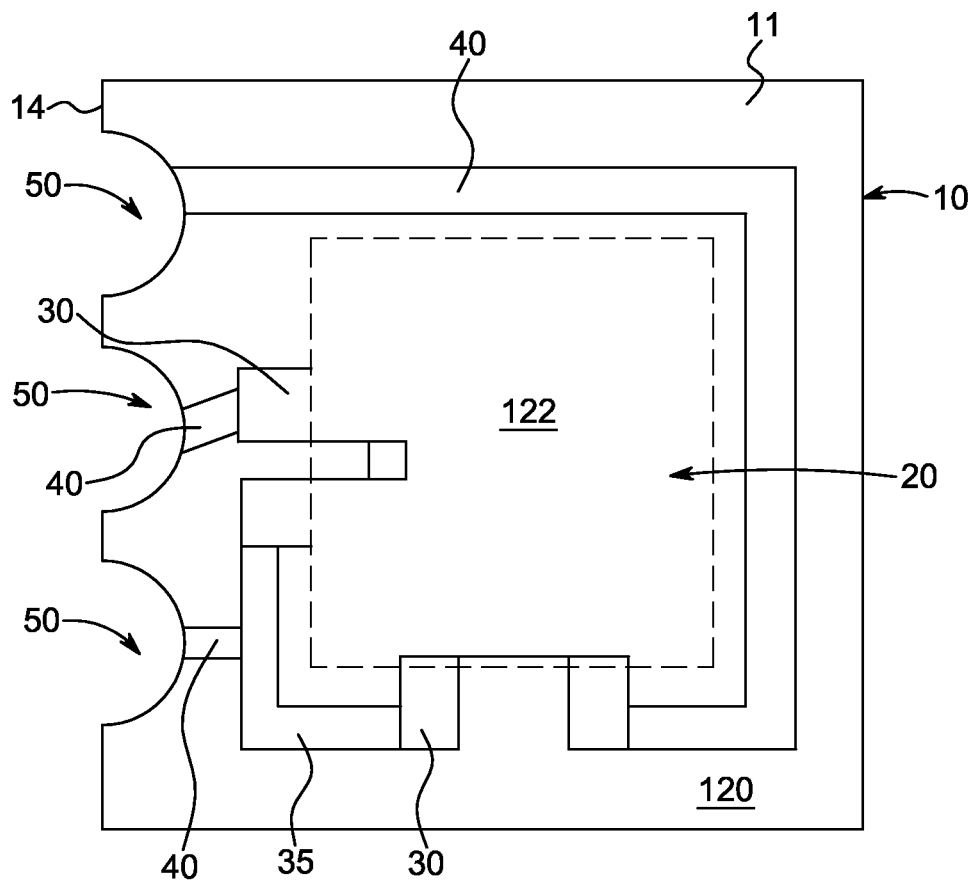
FIG. 2 is an axial view of the catheter die of FIG. 1.

With reference to FIG. 2, at least one or more piezoresistive pressure sensors 30 may be operably disposed at or around the first end face 120 proximate to the diaphragm 122 and the cavity 20. The cavity 20 may be provided as a vacuum or with a known, predefined internal pressure. In either case, when the catheter die 10 is exposed to unknown atmospheric conditions, a pressure differential may exist between an interior of the cavity 20 and an exterior thereof. This pressure differential causes the diaphragm 122 to deform inwardly or outwardly based on which of the interior of the cavity 20 and the exterior thereof has the higher pressure. This deformation of the diaphragm 122 applies a strain to the at least one or more piezoresistive pressure sensors 30 and induces current therein. By coupling appropriate circuitry 35 to the at least one or more piezoresistive pressure sensors 30, a magnitude of this current can be determined. With the pressure within the interior of the cavity 20 known (i.e., either as a vacuum or as a controlled pressure), the pressure at the exterior of the cavity 20 can be calculated from the determined current magnitude.

In accordance with embodiments, it is to be understood that a vent channel that is fluidly communicative with the cavity 20 may be formed to extend substantially longitudinally through the elongate body 11 from, for example, the second end portion 13. Such a vent channel may permit a pressure within the cavity 20 to be actively controlled between a vacuum state and any positive pressure state.

Still referring to FIG. 2, the catheter die 10 may further include at least one or more bond pads 40. Each bond pad 40 may be respectively disposed in electrical communication with each of the at least one or more piezoresistive pressure sensors 30 by way of a portion of the circuitry 35. As described below, each bond pad 40 may include a relatively short portion disposed on the first end face 120 and a relatively long portion disposed to extend longitudinally along at least a portion of one of the sidewalls 14 of the elongate body 11. In accordance with embodiments, the elongate body 11 may be formed with metallized channels 50 defined to extend along at least one or more of the sidewalls 14. In such cases, the relative long portion of each bond pad 40 may extend along a corresponding one of the metalized channels 50.

As shown in FIG. 2, in an exemplary embodiment, a first one of the piezoresistive pressure sensors 30 may be provided on a first edge of the diaphragm 122. An end of a first one of the bond pads 40 may be connected to an input portion of this piezoresistive pressure sensor 30 with a second end of the first bond pad 40 directed along a first one of the metallized channels 50. An output portion of the first piezoresistive pressure sensor 30 is electrically coupled to the circuitry 35. An end of a second one of the bond pads 40 may be connected to the circuitry 35 with a second end of the second bond pad 40 directed along a second one of the metallized channels 50. A second one of the piezoresistive pressure sensors 30 may be disposed in series with the circuitry 35 with a final leg of the circuitry 35 provided as a third one of the bond pads 40. This third bond pad 40 may extend about a periphery of the first end face 120 toward a third one of the metallized channels 50.

Figure 3:
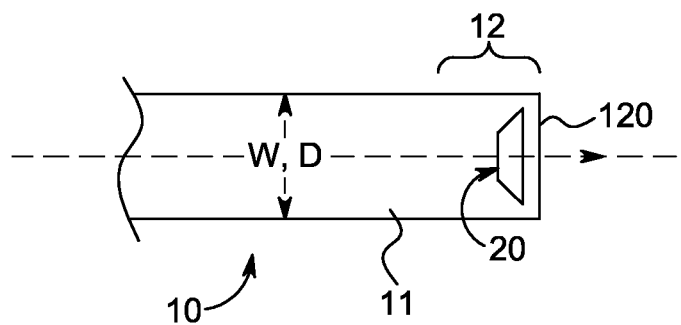
FIG. 3 is a side view of a portion of the catheter die of FIG. 1.
Figure 4:
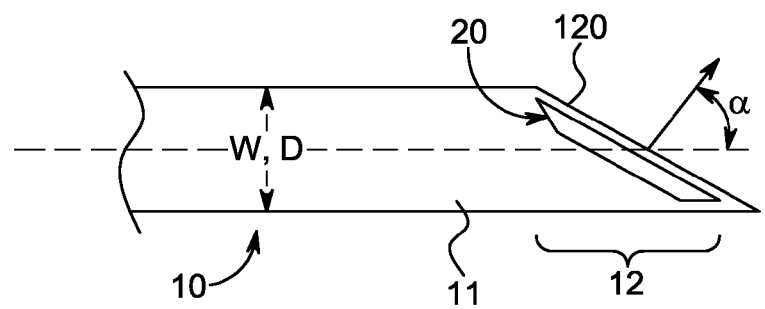
FIG. 4 is a side view of a portion of the catheter die of FIG. 1 in accordance with an alternative embodiment.

With reference now to FIG. 3, where the elongate body 11 is formed as a substantially rectangular volumetric body, the first end face 120 may form a substantially right angle with at least two of the opposing sidewalls 14 such that a normal angle relative to the first end face 120 is substantially aligned with a longitudinal axis of the elongate body 11. By contrast, with reference to FIG. 4, where the elongate body 11 is formed as a substantially trapezoidal or parallelipipedal volumetric body, the first end face 120 may form an obtuse angle with a first one of the sidewalls 14 and an acute angle with a second one of the sidewalls 14, which opposes the first one of the sidewalls 14. In this case, a normal angle relative to the first end face 120 is transversely oriented or angled with respect to the longitudinal axis of the elongate body 11 by an angle, $\alpha$. In each case of FIGS. 3 and 4, the cavity 20 remains disposed proximate to the first end face 120 as described above. However, in the latter case, the dimensions of the end face 120 are extended. As such, in the latter case, the dimensions of the diaphragm 122 and the cavity 20 are similarly extended without the need for an increase an overall width, W, or depth, D, of the elongate body 11. Of course, it is to be understood that the shapes referred to above are merely exemplary and that other shapes for the elongate body 11 as a whole or in cross-section are possible.

With the potential for the first end face 120, the diaphragm and the cavity 20 having such extended "planar" dimensions that do not require corresponding increases in an overall width, W, or depth, D, of the elongate body 11, accuracies of the measurements of the piezoresistive sensors 30 can be correspondingly increased without increasing an overall size of the catheter die 10. This is at least partially due to the fact that, as a size of the diaphragm 122, for example, increases, the diaphragm 122 becomes increasingly sensitive to pressure differentials between the interior of the cavity 20 and the exterior thereof. This increased sensitivity leads to more responsive current induction within the at least one or more piezoresistive pressure sensors 30 and the circuitry 35 and to the more accurate pressure calculations.

With reference to FIGS. 5-8, a method of fabricating a catheter die as described above will be described below. It is to be understood that, for purposes of clarity and brevity, the description will generally relate to the exemplary embodiments of the catheter die 10 shown in FIGS. 1-4. The method of fabricating the catheter die 10 with the vent channel would be substantially similar and need not be separately described.

Figure 5:
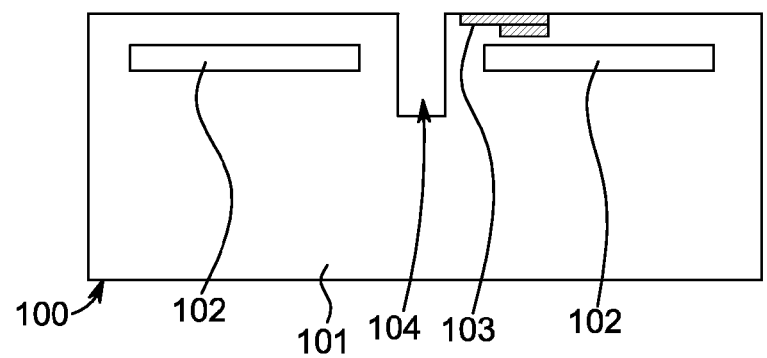
FIG. 5 is a side view of wafer with cavities and a channel defined therein and a piezoresistive pressure sensor formed therein.

As shown in FIG. 5, the method initially includes formation of a wafer 100 having a body 101. In accordance with embodiments, a thickness of the body 101 should be provided such that a catheter die to be formed from the wafer 100 has an elongate body with shape and size characteristics similar to the description provided above.

The wafer 100 may be formed as a silicon-on-insulator (SOI) wafer including an n-type or p-type semi-conductor (i.e., silicon), a buried oxide layer and a handle layer. Multiple cavities 102 are defined in the body 101 by, for example, a wet etch process, such as Potassium Hydroxide (KOH) etching or Tetramethylammonium Hydroxide (TMAH) etching, or a dry etch process, such as Deep Reactive Ion Etching (DRIE). The multiple cavities 102 are defined proximate to an upper surface of the body 101 such that portions of the upper surface are defined as diaphragms to be respectively responsive to pressure differentials between an interior of the corresponding cavity 102 and an exterior. In between adjacent multiple cavities, channels 104 may also be formed by similar wet or dry etch processes.

Still referring to FIG. 5, piezoresistive pressure sensors 103 and interconnect portions thereof are formed in the body 101 such that the piezoresistive pressure sensors 103 are each operably disposed proximate to a corresponding one of the cavities 102. Formation of the piezoresistive pressure sensors 103 and the interconnect portions may include one or more of p-type dopant diffusion and implantation.

Figure 6:
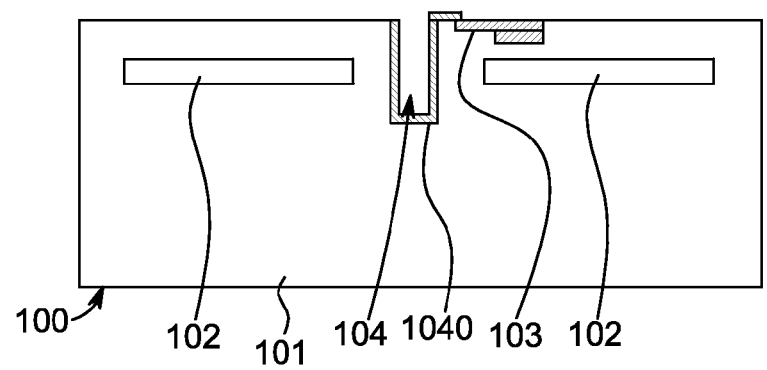
FIG. 6 is a side view of the wafer of FIG. 5 following oxidization processing.
Figure 7:
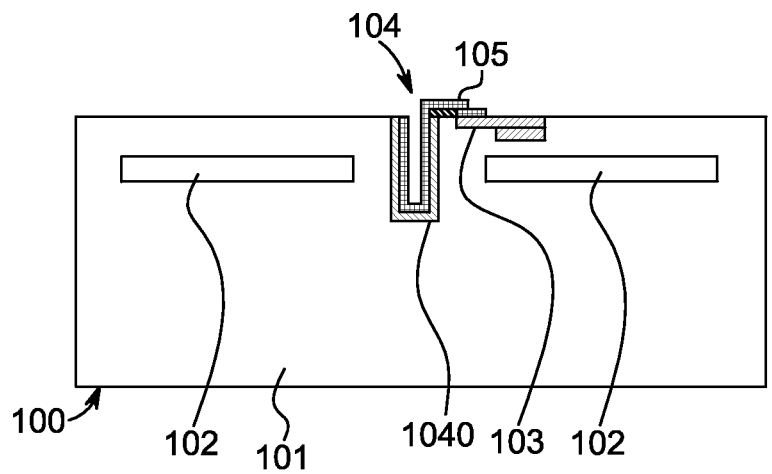
FIG. 7 is a side view of the wafer of FIG. 6 following metallization processing.

As shown in FIGS. 6 and 7, at least the inner surfaces of the channels 104 and portions of the upper surface of the body 101 may be selectively oxidized (see FIG. 6) to form an insulation layer 1040. This selective oxidization processing is then followed by metallization processing (see FIG. 7) to form a bond pad 105. The bond pad 105 is electrically coupled to the interconnect portion of a corresponding one of the piezoresistive pressure sensors 103 and extends into the selectively oxidized channel 104 along the insulation layer 1040. The metallization process may include, for example, deposition processing of a suitable metal or metallic alloy (i.e., aluminum).

Figure 8:
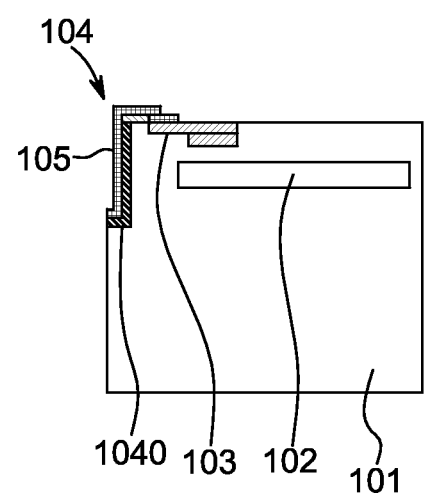
FIG. 8 is a side view of the wafer of FIG. 6 following singulation processing.

With reference to FIG. 8, the method further includes singulation processing. During singulation processing, the wafer 100 is cut into at least one or more catheter dies as described above. The singulation processing may be conducted at the channels 104 such that the cut out catheter die is provided with the remaining portion of the channel 104 disposed along a sidewall thereof and with the bond pad 105 extending longitudinally away from the upper surface of the body 101. Moreover, the singulation processing may include cutting or dicing along right angles with respect to the upper surface of the body 101, as shown in FIG. 8, or along non-right angles (see FIG. 4). In the latter case, the relative sizes of the cavity 102 and the diaphragm of the cut out catheter die as compared to the width and depth of the catheter die as a while will be increased with the concomitant advantages to such a configuration provided as described above.

In accordance with the descriptions provided above, the use of the wafer 100 with the relatively thick body 101 allows for simplified catheter die formation with a reduced risk of failure. Normally, a catheter die will be formed from a relatively thin wafer material that is prone to failures, such as damage or complete breakage, as a result of processing. The wafer 100 with the relatively thick body 101, on the other hand, has additional material that allows the wafer 100 to be stronger and more rigid with an allowance for greater processing tolerances.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Additionally, while various embodiments of the invention have been described, it is to be understood that aspects of the invention may include only some of the described embodiments. Accordingly, the invention is not to be seen as limited by the foregoing description, but is only limited by the scope of the appended claims.

The invention claimed is:

1. A catheter die, comprising:
    an elongate body having a first end portion, a second end portion, and an end face at the first end portion, the elongate body defining a cavity completely enclosed within the first end portion with an interior facing surface of the cavity disposed to extend alongside at least a portion of the end face of the first end portion; and
    at least one or more piezoresistive pressure sensors operably disposed proximate to the cavity.

2. The catheter die according to claim 1, further comprising at least one or more bond pads respectively disposed in electrical communication with the at least one or more piezoresistive pressure sensors.

3. The catheter die according to claim 2, wherein each of the at least one or more bond pads extends along a longitudinal length of the elongate body.

4. The catheter die according to claim 2, wherein each of the at least one or more bond pads extends along a metalized channel formed along a longitudinal length of the elongate body.

5. The catheter die according to claim 1, wherein the end face is about 0.3-0.5 mm by about 0.3-0.5 mm and a longitudinal length of the elongate body is about 0.8-1.2 mm.

6. The catheter die according to claim 1, wherein the cavity is defined as a frusto-trapezoidal volume.

7. The catheter die according to claim 1, wherein the end face is oriented normally with respect to a longitudinal axis of the elongate body.

8. The catheter die according to claim 1, wherein a normal angle of the end face is oriented transversely with respect to a longitudinal axis of the elongate body.

9. A catheter die, comprising:
    an elongate body having sidewalls, longitudinal first and second opposing end portions of the sidewalls and an end face at the longitudinal first end portion,
    the sidewalls having a longitudinal length that is larger than any planar dimension of the end face,
    the elongate body defining a cavity having an interior facing surface proximate to the end face such that a portion of the end face is defined as a diaphragm,
    the interior facing surface being disposed alongside at least a portion of the end face; and
    at least one or more piezoresistive pressure sensors operably disposed proximate to the diaphragm and the cavity.

10. The catheter die according to claim 9, further comprising at least one or more bond pads respectively disposed in electrical communication with the at least one or more piezoresistive pressure sensors.

11. The catheter die according to claim 10, wherein each of the at least one or more bond pads extends along at least a portion of one of the sidewalls.

12. The catheter die according to claim 10, wherein each of the at least one or more bond pads extends along a metalized channel formed in at least a portion of one of the sidewalls.

13. The catheter die according to claim 9, wherein the end face is about 0.3-0.5 mm by about 0.3-0.5 mm and at least one of the sidewalls is about 0.3-0.5 mm by about 0.8-1.2 mm.

14. The catheter die according to claim 9, wherein a magnitude of the longitudinal length is about 2.5-3.0 times a magnitude of any planar dimension of the end face.

15. The catheter die according to claim 9, wherein the cavity is defined as a frusto-trapezoidal volume.

16. The catheter die according to claim 9, wherein the end face forms a right angle with at least two opposing sidewalls.

17. The catheter die according to claim 9, wherein the end face forms an obtuse angle with a first one of the sidewalls and an acute angle with a second one of the sidewalls, which opposes the first one of the sidewalls.

18. A method of assembling a catheter die, comprising:
    forming an elongate body having a first end portion, a second end portion opposing the first end portion, and an end face at the first end portion, the elongate body having a longitudinal length that is larger than any planar dimension of the end face;
    defining a cavity completely enclosed within the first end portion such that an interior facing surface of the cavity is disposed alongside at least a portion of the end face; and operably disposing a piezoresistive pressure sensor proximate to the cavity.

19. The method according to claim 18, wherein the forming comprises forming a metalized channel along a longitudinal length of the elongate body, and the method further comprises disposing a bond pad along the metalized channel and in electrical communication with the piezoresistive pressure sensor.

20. The method according to claim 18, wherein the end face is oriented one of substantially normally with respect to a longitudinal axis of the elongate body or transversely with respect to a longitudinal axis of the elongate body.

21. The catheter die according to claim 1, wherein the interior facing surface is proximate to the end face such that a portion of the end face is defined as a diaphragm.

22. The method according to claim 18, wherein the interior facing surface is proximate to the end face such that a portion of the end face is defined as a diaphragm.

23. A method of detecting pressure, comprising:
(a) providing a catheter die comprising:
    an elongate body having first and second opposing end portions and an end face at the first end portion, the elongate body defining a cavity within the first end portion with an interior facing surface of the cavity disposed to extend alongside at least a portion of the end face of the first end portion, wherein the interior facing surface is proximate to the end face such that a portion of the end face is defined as a diaphragm which deforms in accordance with a pressure differential between an interior of the cavity and an exterior of the cavity; and
    at least one or more piezoresistive pressure sensors operably disposed proximate to the cavity such that said at least one or more piezoelectric pressure sensors experience strain when the diaphragm deforms;
(b) exposing the catheter die to the pressure to be measured to cause the diaphragm to deform in accordance with the pressure differential; and
(c) detecting the pressure using the at least one or more piezoresistive pressure sensors.

* * * * *